United States Patent [19]
Williams et al.

[11] Patent Number: 6,020,110
[45] Date of Patent: Feb. 1, 2000

[54] PRODUCTION OF ELECTRODES FOR ELECTROCHEMICAL SENSING

[75] Inventors: Stephen Charles Williams; Peter Thomas Arnold; Bernadette Yon-Hin, all of Cambridge, United Kingdom

[73] Assignee: Cambridge Sensors Ltd., United Kingdom

[21] Appl. No.: 08/765,565
[22] PCT Filed: Jun. 23, 1995
[86] PCT No.: PCT/GB95/01476
   § 371 Date: Jan. 27, 1997
   § 102(e) Date: Jan. 27, 1997
[87] PCT Pub. No.: WO96/14769
   PCT Pub. Date: May 23, 1996

[30] Foreign Application Priority Data

Jun. 24, 1994 [GB] United Kingdom ............. 9412789

[51] Int. Cl.⁷ ......................................... G03F 7/26
[52] U.S. Cl. ............................... 430/315; 430/311
[58] Field of Search ............................ 430/311, 315

[56] References Cited

FOREIGN PATENT DOCUMENTS

| | | |
|---|---|---|
| 0230472 | 12/1986 | European Pat. Off. . |
| WO 8606484 | 11/1986 | WIPO . |
| WO 91/08474 | 6/1991 | WIPO . |
| WO 9108474 | 6/1991 | WIPO . |

OTHER PUBLICATIONS

Aoki et al. "Diffusion Controlled Current at a Stationary Finite Disk Electrode." J. Electroanal. Chem., vol. 125, 315–320, 1981.

J. Electroanal. Chem., vol. 125, 315–320 (1981).

Analytical Chemistry, vol. 62, 2206–2210 (1990).

Analytical Chemistry, vol. 63, 931–936 (1991).

*Primary Examiner*—Kathleen Duda
*Attorney, Agent, or Firm*—Ohlandt, Greeley, Ruggiero & Perle, LLP; George W. Rauchfuss, Jr.

[57] ABSTRACT

A method for the production of electrodes, especially microelectrodes, in which the (micro) electrode consists essentially of an electrically-insulating material through which apertures are formed to reveal the electrically-conducting material, is characterized in that aperture as formed by the use of a light-hardened (photopolymerizing) resist or light-softened (photoinduced breaking of bonds) resist.

9 Claims, 2 Drawing Sheets

PRODUCTION OF ELECTRODES FOR ELECTROCHEMICAL SENSING

This application is a 35 U.S.C. 371 filing based on PCT/GB 95/01476 filed Jun. 23, 1995.

FIELD OF THE INVENTION

This invention relates to the fabrication of electrodes for use in an electrochemical test method for a species being detected.

BACKGROUND OF THE INVENTION

There is considerable demand for the testing of species using electrochemical methods. These species include but are not limited to metals, glucose, biochemical species, gases and other redox species. Analysis of these species may be achieved at conventional large electrodes or at microelectrodes. The latter offer improved precision, sensitivity, improved signal to noise ratios, reduced interference from interfering species such as oxygen, and in addition the potential to measure species in highly resistive media. Therefore a considerable effort has been expended on methods to produce these electrodes in a well-defined microelectrode array format that retains all the advantages of single microelectrodes and provides higher currents compared to those obtainable at individual microelectrodes (pA-nA).

Existing methods of fabrication for these electrodes are either by hand using epoxy resin encapsulation (W. L. Caudill et al, Anal. Chem. (1982) 54:2532) which is too time consuming and inefficient, or require expensive equipment, as in the case of fabrication by photo-ablation with lasers (WO-A-9108474) and electron beam etching techniques (M. S. Wrighton, Science (1986) 231:32). Other methods such as fabrication by the adhesion of microporous membranes (J. Wang and J. M. Zadeii, J. Electroanal. Chem. (1988) 249:339) failed due to heterogeneity in the arrangement of the pores resulting in poor reproducibility. J.Osteryoung and T. Hempel, J. Electrochem. Soc. (1986) 133:757, have investigated the use of thin film techniques but these have failed due to adhesion problems between the layers.

An object behind the present invention is to produce a satisfactory microelectrode array at low cost.

SUMMARY OF THE INVENTION

According to the invention, a method for making a microelectrode comprising a layer of apertures through an electrically-insulating layer to reveal an electrically-conducting layer, is characterised by the fact that the apertures are made by photoimaging (the use of substances that can be polymerized by the application of light or the use of substances that can have their bonds broken by the application of light). These light-sensitive materials are also known as photoimageable resists. Their use provides a convenient, economic process for the fabrication of products having properties comparable to those made by more expensive methods. An electrode produced by the method of the invention is suitable for use in analytical methods for the detection of species by an electrochemical reaction, and for incorporation in a suitable instrument.

DESCRIPTION OF THE INVENTION

In one embodiment of the invention, the microelectrode consists essentially of a conducting electrode material deposited on a non-conducting substrate. The substrate may be a polymer layer such as polyester, polycarbonate or polyvinyl chloride.

The conducting material of the electrode layer is not critical. It may be a carbon, gold or another metal in a printable ink formulation or another formulation that is suitable for the chosen deposition process. The electrode material may be deposited on the substrate by a conventional process including, but not limited to, thick film printing (also known as silk screen printing), lithography, vapour deposition, spray-coating, roller-coating or vacuum deposition.

A photoimageable dielectric layer, such as a photoimageable negative resist is then deposited over the conducting electrode material by a second process. This again may be conventional, such as vapour deposition, silk screen printing, spin coating, or lithographic printing.

An image of the required array is then held at the surface of the electrode, and the system is exposed to suitable light source for an appropriate period. The photoimageable layer is then photopolymerised by the light source in those areas that are exposed. In areas that are covered by the mask, the photoimagable layer remains unpolymerized. The mask is therefore designed to cover those areas of the resist that are to be dissolved away by the developer in the next step.

The electrode is then exposed for an appropriate period to developing solution which dissolves away those areas where the photoimageable layer has not polymerised, to reveal the layer below. In this manner a regular array of apertures can be constructed.

In an alternative embodiment of the invention, the same substrate and conducting layer are used but with a positive photoimageable resist (in this case, the bonds between molecules in the resist are broken when the light is applied). In this case, the positive resist is applied to the electrode by the chosen process and a mask is placed over the coated electrode. The mask is designed to expose those areas of the resist that are to be dissolved away by the developer in the next stage. The assembly is exposed to the light source and those areas of the resist exposed to the light have intermolecular bonds broken by the light, thereby rendering them soluble in the developing solution used in the next step. Unexposed areas of resist remain unaffected and resistant to the developer.

The electrode is then exposed to the developing solution and the resist is dissolved away by the developer in the exposed areas to reveal the array.

An alternative method of fabricating the microelectrode involves the use of dry freestanding photoimageable film resists, e.g. 5–50 μm. An array of apertures at these film resists, as described by the above procedures, may be formed either before or after the application of the conducting material. The coated sheet can then be bonded to a non-conducting substrate, conducting side down, to provide rigidity to the electrode.

In all these processes, resists are chosen that are capable of being developed in mild solutions (aqueous or non-aqueous) that will not damage other exposed areas of the electrode. Alternatively, masks can be applied to the electrodes to protect very sensitive parts of the electrodes from the developing solutions.

The equipment required for the process is low cost and readily available, and comprises a light source, development unit and deposition equipment. A preferred embodiment has both the electrode material and the resist deposited by thick film printing processes which are low cost and high volume. Several electrodes can be fabricated at once, lending the process to high volume low cost production which is required for many industrial applications.

Electrodes fabricated by this method have several characteristics that are desirable for their use in the analysis of species including:

1. A regular array of electrodes can be produced of uniform size and shape. The diameter of the apertures may vary in the range 10–75 μm at regular spacing. A typical spacing will be apertures regularly spaced in the range 2–10 aperture diameters apart.
2. Various materials can be used for the construction of the layers underneath the non-conducting layer, including gold, metals, carbon, platinum etc. These layers may be modified to enhance the attachment of additional molecules as described in (3).
3. Once the apertures have been formed, further processing may be used to further modify the electrode apertures for analysis, including deposition or bonding or absorption of metals, enzymes, specific binding partners (including, but not limited to, antibodies, antigens, DNA or RNA, avidin, biotin, gene probes) and catalysts.
4. By arranging the electrically-conducting layer appropriately, the individual apertures may be addressed at different potentials to analyze interferences or analyze different species. In addition, the individual microelectrodes may be electrically modified with different redox species or polymers to provide specificity and allow multi-analyte measurements.
5. The apertures can be of any shape including circles, squares, rectangles or bands. The latter shapes can be used to form microband electrodes.
6. In order to facilitate the analysis and speed it up, the electrically-conducting layer may be heated so as to facilitate chemical reactions at the electrode surfaces. This may be particularly useful with the detection of gases.

The electrodes are sufficiently cheap to be used once and discarded, thereby preventing carryover or memory problems between analyses. Alternatively, the electrode may be reused for future analysis in cases where carryover is not problematic.

The microelectrodes may be used with a small portable potentiostat or galvanostat to poise the working potentials at the required levels. In this manner, a complete portable system may be constructed for field analysis of species. The output from the instrument is proportional to the level of the analyte in solution or in a gas.

An assay device may comprise a working electrode comprising microelectrodes made by the method of the invention, a suitable counter-electrode chosen from a similar range of material as given for the conducting layer of the microelectrode, and a silver/silver chloride reference electrode. The microelectrode may be electroplated with a mercury or gold film before use in the analysis of heavy metals.

The device may also include a sample cell or porous layer to wick a sample onto the microelectrode from a container. The sample cell or porous layer may also contain buffers and/or other reagents to pre-treat the sample before it arrives at the microelectrode apertures. For instance, in testing for the presence of heavy metals in water, the sample cell or porous layer may include a buffer salt, a mercurous or gold salt and any other dried reactants for electroplating. The assay device in accordance with this aspect of the invention may be used as a disposable unit which is plugged into a suitable potentiostat or galvanostat to carry out the required measurement using traditional electrochemical techniques.

BRIEF DESCRIPTION OF THE DRAWINGS

The invention will be described by way of example only with reference to the following Example and the accompanying drawings, in which.

EXAMPLE

Figure 1:
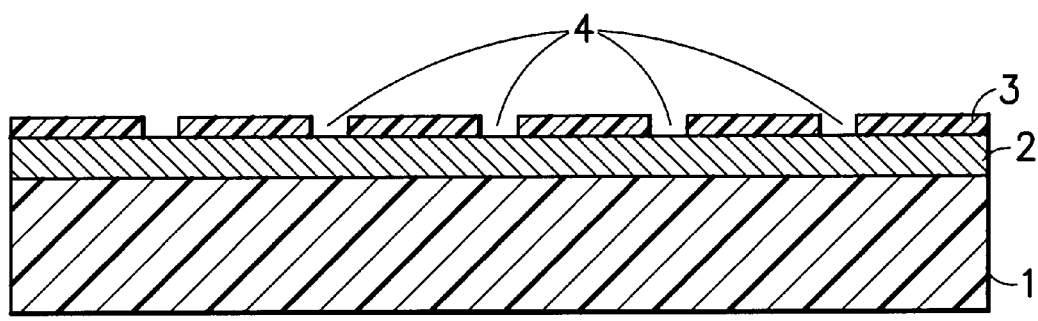
FIG. 1 is a cross-sectional view of part of a microelectrode array produced according to the invention.
Figure 2:
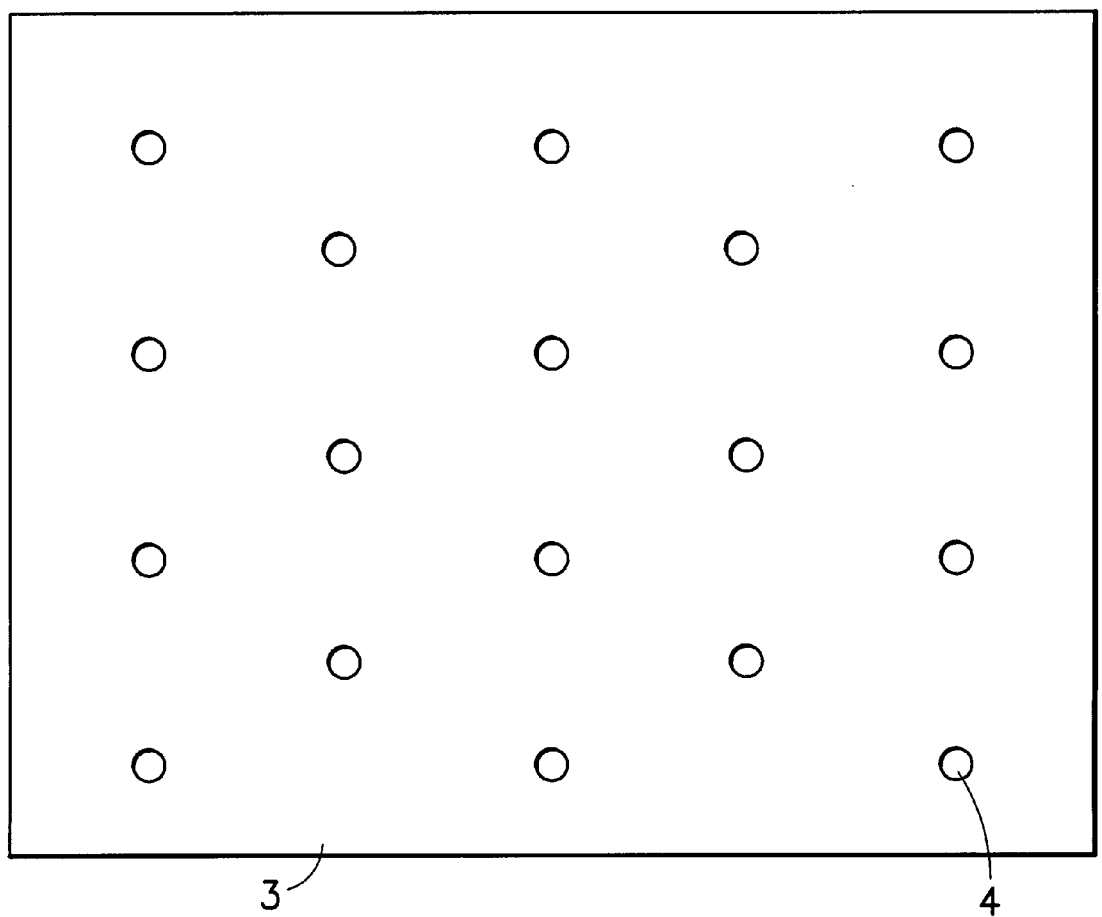
FIG. 2 is a top view of the array shown in FIG. 1.

An electrode as shown in FIGS. 1 and 2 is constructed from a substrate 1 that is a 250 μm thick polyester sheet, a conducting layer 2 that is a screen-printable carbon ink, and a negative photoimagable resist 3 that is Imagecure AQ™ (Coates Circuit Products). The photoimagable resist is printed over the conducting layer 2 and baked in an oven at 80° C. for 10 minutes. An array of apertures 4 is patterned onto the resist by exposure to a 3 kW light source unit for 7 seconds through an appropriate mask. The apertures are revealed by removing the unexposed resist in a 1% sodium carbonate solution. The sheet is subjected to a final cure at 100° C. for 60 minutes. The result is a series of circular discs 18 μm in diameter, spaced at 180 μm between the centres. In addition, the discs are located at the centres of a hexagonal array and the array has a total of 540 of these discs over the working electrode area.

The assay device comprises the working, reference and counter electrodes, produced on a flat polyester substrate. The working and counter electrodes are printed carbon inks and the reference electrode is a printed silver/silver chloride reference electrode next to the microarray working electrode. In one convenient format, a sample cell is formed above the electrodes by a polyester film using a spacer 250–300 μm thick. An opening at one end of the compartment allows the test sample to fill the cell and another opening at the other end of the cell allows air to be expelled from the cell. Hence, a well-defined volume of sample resides in the cell during measurements. The cell can be pre-coated with reagents including buffers and/or redox species so that on rehydration in the sample liquid, the dried reagents are dispersed throughout the test liquid and the test liquid is maintained at the correct pH.

Figure 3:
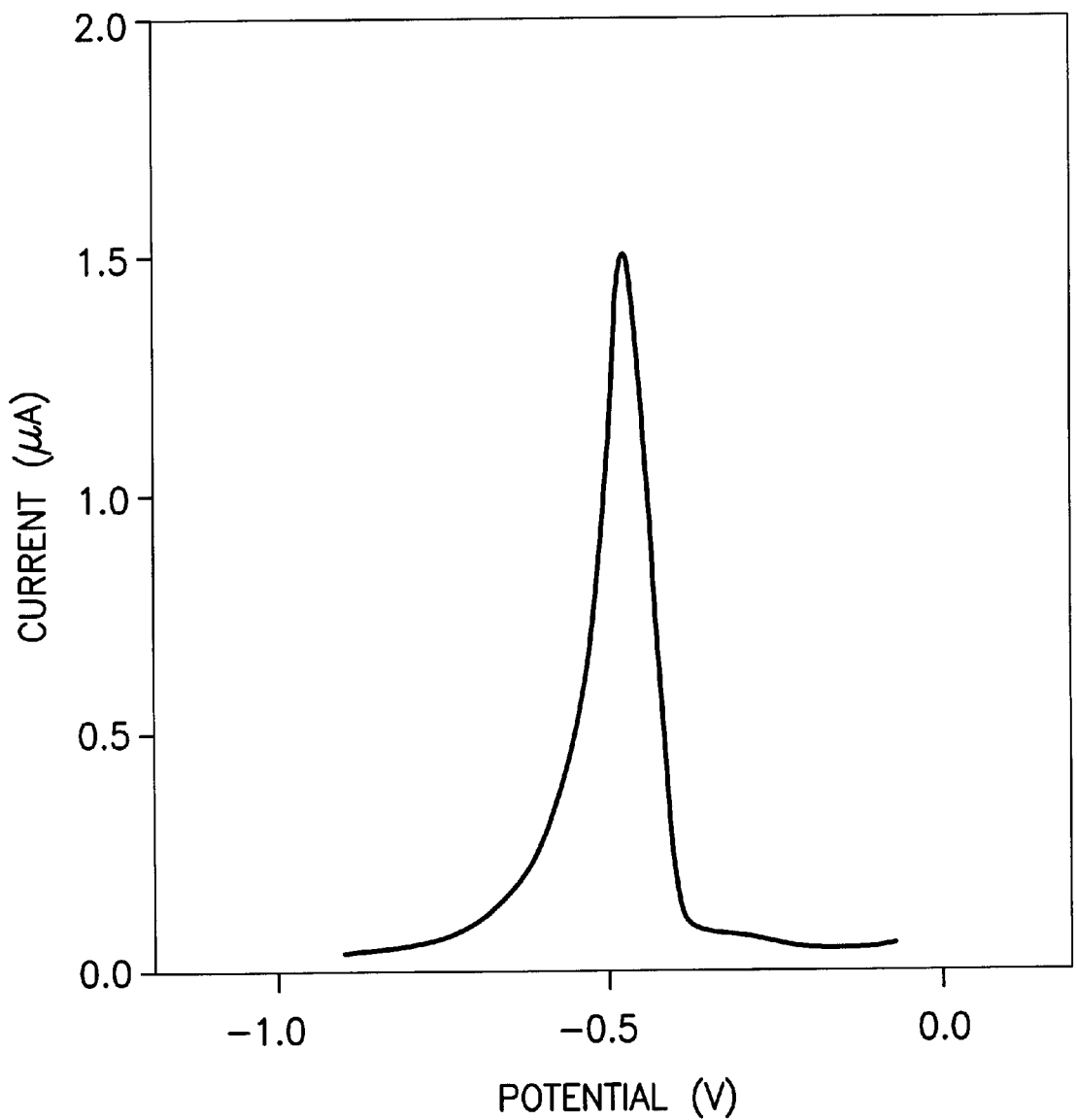
FIG. 3 is a graph showing a trace obtained in use of a device incorporating an embodiment of the invention, for the analysis of a test liquid containing lead.

When poised at suitable potentials against the reference electrode, the working microelectrode can be used for the analysis of heavy metals in solution. The heavy metal ions are first plated onto the microelectrode by applying a sufficiently cathodic potential and maintaining the plating current at the microelectrode for a fixed length of time (typically 2–5 minutes), in order to plate a measurable amount of heavy metals at the microconducting areas. The plated heavy metals are re-oxidised at the microelectrode by anodic stripping voltammetry, resulting in a plot of current against voltage (FIG. 3). The peak current output is directly proportional to the concentration of the heavy metal, and the voltage at which the peak appears is metal ion-specific.

We claim:

1. A method for producing a microelectrode, which comprises depositing an electrically-conducting layer on a non-conducting polymeric plastic substrate by thick film printing;

applying on the conducting layer an electrically-insulating layer of photoimageable dielectric material; and forming in the insulating layer, before or after application of the insulating layer onto the conducting layer, an array of apertures that expose the conducting layer, the apertures being formed by image-wise exposing the electrically-insulating layer of dielectric material to render parts of the insulating layer removable, followed by developing with a developer solution to remove said parts to form the array of apertures.

2. A method according to claim 1, wherein the dielectric material is exposed image-wise to render parts of the dielectric material removable, and said parts of the dielectric layer are removed by a developer, to form the array after application of the insulating layer on the conducting layer.

3. A method according to claim 1, wherein the dielectric material is photoimaged to produce the array of apertures, prior to bonding of the dielectric material to the conducting layer.

4. A method according to claim 1, wherein the apertures are of uniform size and shape, and are regularly-spaced, their diameters being 10 to 75 $\mu$m.

5. A method according to claim 1, wherein the apertures are regularly spaced, 2 to 10 aperture diameters apart.

6. A method according to claim 1, which additionally comprises deposition of a metal species to the exposed conducting layer.

7. A method according to claim 6, wherein the metal species is selected from the group consisting of gold, mercury and platinum.

8. A method according to claim 1, which additionally comprises bonding or adsorption of proteins, nucleic acids, small molecules or conducting polymers to the exposed conducting layer.

9. A method for producing a microelectrode, which method comprises:

(a) providing a non-conducting polymeric plastic substrate;

(b) depositing on said plastic substrate an electrically-conducting layer;

(c) applying on the electrically-conducting layer an electrically insulating photoimageable resist layer, and (d) before or after application of the electrically insulating layer on the electrically-conducting layer, forming an array of apertures in the electrically insulating photoimageable resist layer, for exposing the electrically-conducting layer on the plastic substrate, by image-wise exposure of said resist layer to a light source through a patterned mask to render portions of said resist layer removable by a developer and thereafter contacting the resist layer with developer to remove said removable portions of the resist layer.

* * * * *